United States Patent
Fuller et al.

(10) Patent No.: US 10,519,149 B2
(45) Date of Patent: *Dec. 31, 2019

(54) BICYCLIC INHIBITORS OF HISTONE DEACETYLASE

(71) Applicant: Rodin Therapeutics, Inc., Boston, MA (US)

(72) Inventors: Nathan Oliver Fuller, Arlington, MA (US); John A. Lowe, III, Stonington, CT (US)

(73) Assignee: Rodin Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,299

(22) Filed: Mar. 23, 2018

(65) Prior Publication Data

US 2018/0215759 A1    Aug. 2, 2018

Related U.S. Application Data

(63) Continuation of application No. 15/867,982, filed on Jan. 11, 2018, now Pat. No. 9,951,069.

(60) Provisional application No. 62/555,298, filed on Sep. 7, 2017, provisional application No. 62/445,022, filed on Jan. 11, 2017.

(51) Int. Cl.
*C07D 471/04* (2006.01)
*A61K 31/437* (2006.01)
*A61K 31/519* (2006.01)
*A61P 25/28* (2006.01)

(52) U.S. Cl.
CPC .......... *C07D 471/04* (2013.01); *A61K 31/437* (2013.01); *A61K 31/519* (2013.01); *A61P 25/28* (2018.01)

(58) Field of Classification Search
CPC ..... A61K 31/437; A61K 31/519; A61P 25/28; C07D 471/04
See application file for complete search history.

(56) References Cited

U.S. PATENT DOCUMENTS

| | | | |
|---|---|---|---|
| 5,112,824 A | 5/1992 | Baldwin et al. |
| 5,872,136 A | 2/1999 | Anthony et al. |
| 7,544,695 B2 | 6/2009 | Berk et al. |
| 7,834,026 B2 | 11/2010 | Berk et al. |
| 7,863,279 B2 | 1/2011 | Even et al. |
| 7,981,874 B2 | 7/2011 | Close et al. |
| 8,349,825 B2 | 1/2013 | Mampreian et al. |
| 8,461,189 B2 | 6/2013 | Heidebrecht, Jr. et al. |
| 8,686,020 B2 | 4/2014 | Hamblett et al. |
| 8,703,959 B2 | 4/2014 | Kutose et al. |
| 8,809,544 B2 | 8/2014 | Kutose et al. |
| 8,962,849 B2 | 2/2015 | Kutose et al. |
| 8,962,850 B2 | 2/2015 | Kutose et al. |
| 8,981,107 B2 | 3/2015 | Kutose et al. |
| 9,951,069 B1 | 4/2018 | Fuller et al. |
| 2002/0183324 A1 | 12/2002 | Jacobson et al. |
| 2003/0187026 A1 | 10/2003 | Li et al. |
| 2003/0199511 A1 | 10/2003 | Li et al. |
| 2005/0025995 A1 | 2/2005 | Cheng et al. |
| 2005/0153981 A1 | 7/2005 | Li et al. |
| 2005/0245530 A1 | 11/2005 | Borzilleri et al. |
| 2006/0173050 A1 | 8/2006 | Liu et al. |
| 2006/0235028 A1 | 10/2006 | Li et al. |
| 2006/0270686 A1 | 11/2006 | Kelly et al. |
| 2007/0004741 A1 | 1/2007 | Apodaca et al. |
| 2007/0037794 A1 | 2/2007 | Ungashe et al. |
| 2007/0135437 A1 | 6/2007 | Benjamin et al. |
| 2008/0064871 A1 | 3/2008 | Hirata et al. |
| 2008/0103182 A1 | 5/2008 | Ackermann et al. |
| 2008/0132503 A1 | 6/2008 | Moradei et al. |
| 2008/0280891 A1 | 11/2008 | Kelly et al. |
| 2009/0022047 A1 | 1/2009 | Seto et al. |
| 2009/0058982 A1 | 3/2009 | Seto et al. |
| 2009/0062297 A1 | 3/2009 | Heidebrecht et al. |
| 2009/0156825 A1 | 6/2009 | Heidebrecht, Jr. et al. |
| 2009/0207712 A1 | 8/2009 | Seto et al. |
| 2009/0286782 A1 | 11/2009 | Ibrahim et al. |
| 2009/0286783 A1 | 11/2009 | Ibrahim et al. |
| 2009/0306086 A1 | 12/2009 | Ibrahim et al. |
| 2009/0306087 A1 | 12/2009 | Ibrahim et al. |
| 2010/0041670 A1 | 2/2010 | Even et al. |
| 2010/0099676 A1 | 4/2010 | Endoh et al. |
| 2011/0009365 A1 | 1/2011 | Dubois et al. |
| 2011/0021494 A1 | 1/2011 | Maier et al. |
| 2011/0105472 A1 | 5/2011 | Greul et al. |
| 2011/0118248 A1 | 5/2011 | Ungashe et al. |

(Continued)

FOREIGN PATENT DOCUMENTS

| | | |
|---|---|---|
| CN | 103601718 A | 2/2014 |
| CN | 103864754 A | 6/2014 |
| CN | 105777632 A | 7/2016 |
| CN | 106946890 A | 7/2017 |
| DE | 4212748 A1 | 10/1993 |
| EP | 2712655 A1 | 4/2014 |
| GB | 2515785 A | 1/2015 |
| GB | 2516303 A | 1/2015 |
| JP | H11-049676 A | 2/1999 |
| JP | H11-209366 A | 8/1999 |

(Continued)

OTHER PUBLICATIONS

Johnson et al., (British J. of Cancer 2001, p. 1424-1431) (Year: 2001).*

(Continued)

*Primary Examiner* — Umamaheswari Ramachandran
(74) *Attorney, Agent, or Firm* — McCarter & English, LLP; Steven G. Davis; Michael J. DeGrazia

(57) ABSTRACT

Provided herein are compounds and pharmaceutically acceptable salts thereof, and pharmaceutical compositions thereof, which are useful in the treatment of conditions associated with inhibition of HDAC (e.g., HDAC2).

3 Claims, No Drawings

(56) References Cited

U.S. PATENT DOCUMENTS

| | | |
|---|---|---|
| 2011/0224155 A1 | 9/2011 | Tachdjian et al. |
| 2012/0184572 A1 | 7/2012 | Song et al. |
| 2012/0295881 A1 | 11/2012 | Lange et al. |
| 2013/0210880 A1 | 8/2013 | Amberg et al. |
| 2013/0331382 A1 | 12/2013 | Hubbard et al. |
| 2014/0128391 A1 | 5/2014 | van Duzer et al. |
| 2014/0187780 A1 | 7/2014 | Kim et al. |
| 2014/0329684 A1 | 11/2014 | Muller et al. |
| 2014/0364605 A1 | 12/2014 | Li et al. |
| 2015/0057300 A1 | 2/2015 | Tafesse et al. |
| 2015/0094329 A1 | 4/2015 | Nokura et al. |
| 2015/0266866 A1 | 9/2015 | Conn et al. |
| 2015/0322076 A1 | 11/2015 | Chen et al. |
| 2016/0096833 A1 | 4/2016 | Emmitte et al. |
| 2018/0009818 A1 | 1/2018 | Miyazaki et al. |
| 2018/0194760 A1 | 7/2018 | Jefson et al. |
| 2018/0194769 A1 | 7/2018 | Jefson et al. |

FOREIGN PATENT DOCUMENTS

| | | |
|---|---|---|
| JP | 2003-192673 A | 7/2003 |
| JP | 2003-300940 A | 10/2003 |
| JP | 2008-179067 A | 8/2008 |
| JP | 2008-179068 A | 8/2008 |
| JP | 2009-023986 A | 2/2009 |
| JP | 2009-209090 A | 9/2009 |
| JP | 2012-107001 A | 6/2012 |
| JP | 2013-020223 A | 1/2013 |
| JP | 5-208961 B2 | 6/2013 |
| JP | 2014-101353 A | 6/2014 |
| WO | 1992/01675 A2 | 2/1992 |
| WO | 1996/11929 A1 | 4/1996 |
| WO | 1996/11930 A1 | 4/1996 |
| WO | 1996/18617 A1 | 6/1996 |
| WO | 1996/21660 A1 | 7/1996 |
| WO | 1996/23783 A1 | 8/1996 |
| WO | 1996/32938 A1 | 10/1996 |
| WO | 1997/08167 A1 | 3/1997 |
| WO | 1997/15557 A1 | 5/1997 |
| WO | 1997/36901 A1 | 10/1997 |
| WO | 1998/55472 A1 | 12/1998 |
| WO | 1999/65897 A1 | 12/1999 |
| WO | 2000/002860 A1 | 1/2000 |
| WO | 2000/055114 A1 | 9/2000 |
| WO | 2001/021597 A1 | 3/2001 |
| WO | 2002/014315 A2 | 2/2002 |
| WO | 2002/020011 A2 | 3/2002 |
| WO | 2002/026708 A1 | 4/2002 |
| WO | 2002/032900 A2 | 4/2002 |
| WO | 2002/046172 A2 | 6/2002 |
| WO | 2002/053160 A1 | 7/2002 |
| WO | 2002/068417 A2 | 9/2002 |
| WO | 2002/089738 A2 | 11/2002 |
| WO | 2003/042190 A1 | 5/2003 |
| WO | 2003/051366 A2 | 6/2003 |
| WO | 2003/055447 A2 | 7/2003 |
| WO | 2003/059269 A2 | 7/2003 |
| WO | 2003/062224 A1 | 7/2003 |
| WO | 2003/095437 A1 | 11/2003 |
| WO | 2004/000318 A2 | 12/2003 |
| WO | 2004/000820 A2 | 12/2003 |
| WO | 2004/016597 A2 | 2/2004 |
| WO | 2004/045518 A2 | 6/2004 |
| WO | 2004/071426 A2 | 8/2004 |
| WO | 2004/072033 A2 | 8/2004 |
| WO | 2005/009988 A1 | 2/2005 |
| WO | 2005/014580 A1 | 2/2005 |
| WO | 2005/016862 A1 | 2/2005 |
| WO | 2005/079802 A1 | 9/2005 |
| WO | 2005/095386 A1 | 10/2005 |
| WO | 2005/097740 A1 | 10/2005 |
| WO | 2005/121093 A1 | 12/2005 |
| WO | 2006/019833 A1 | 2/2006 |
| WO | 2006/044975 A2 | 4/2006 |
| WO | 2006/051311 A1 | 5/2006 |
| WO | 2006/065479 A2 | 6/2006 |
| WO | 2006/067445 A2 | 6/2006 |
| WO | 2006/067446 A1 | 6/2006 |
| WO | 2006/076644 A2 | 7/2006 |
| WO | 2006/077168 A1 | 7/2006 |
| WO | 2006/080884 A1 | 8/2006 |
| WO | 2006/084017 A2 | 8/2006 |
| WO | 2006/120133 A2 | 11/2006 |
| WO | 2006/128129 A2 | 11/2006 |
| WO | 2006/128172 A2 | 11/2006 |
| WO | 2006/130403 A1 | 12/2006 |
| WO | 2006/135604 A2 | 12/2006 |
| WO | 2006/137772 A1 | 12/2006 |
| WO | 2007/002313 A2 | 1/2007 |
| WO | 2007/008541 A2 | 1/2007 |
| WO | 2007/049158 A2 | 5/2007 |
| WO | 2007/050980 A2 | 5/2007 |
| WO | 2007/055374 A1 | 5/2007 |
| WO | 2007/056341 A1 | 5/2007 |
| WO | 2007/061880 A1 | 5/2007 |
| WO | 2007/061978 A1 | 5/2007 |
| WO | 2007/064797 A2 | 6/2007 |
| WO | 2007/071598 A1 | 6/2007 |
| WO | 2007/087129 A2 | 8/2007 |
| WO | 2007/087130 A2 | 8/2007 |
| WO | 2007/118137 A1 | 10/2007 |
| WO | 2007/119463 A1 | 10/2007 |
| WO | 2007/122830 A1 | 11/2007 |
| WO | 2007/125984 A1 | 11/2007 |
| WO | 2007/126765 A2 | 11/2007 |
| WO | 2007/129044 A1 | 11/2007 |
| WO | 2007/129052 A1 | 11/2007 |
| WO | 2007/138072 A2 | 12/2007 |
| WO | 2007/139002 A1 | 12/2007 |
| WO | 2007/143557 A2 | 12/2007 |
| WO | 2008/005457 A2 | 1/2008 |
| WO | 2008/009963 A2 | 1/2008 |
| WO | 2008/010985 A2 | 1/2008 |
| WO | 2008/011611 A2 | 1/2008 |
| WO | 2008/012418 A1 | 1/2008 |
| WO | 2008/013963 A2 | 1/2008 |
| WO | 2008/016643 A2 | 2/2008 |
| WO | 2008/024970 A2 | 2/2008 |
| WO | 2008/024978 A2 | 2/2008 |
| WO | 2008/036272 A1 | 3/2008 |
| WO | 2008/047229 A2 | 4/2008 |
| WO | 2008/053913 A1 | 5/2008 |
| WO | 2008/067874 A1 | 6/2008 |
| WO | 2008/074788 A1 | 6/2008 |
| WO | 2008/078837 A1 | 7/2008 |
| WO | 2008/092199 A1 | 8/2008 |
| WO | 2008/093024 A2 | 8/2008 |
| WO | 2008/115262 A2 | 9/2008 |
| WO | 2008/115719 A1 | 9/2008 |
| WO | 2008/119015 A2 | 10/2008 |
| WO | 2008/129280 A1 | 10/2008 |
| WO | 2008/139152 A1 | 11/2008 |
| WO | 2008/145843 A1 | 12/2008 |
| WO | 2008/151184 A1 | 12/2008 |
| WO | 2008/151211 A1 | 12/2008 |
| WO | 2008/154221 A2 | 12/2008 |
| WO | 2009/005638 A2 | 1/2009 |
| WO | 2009/022171 A1 | 2/2009 |
| WO | 2009/032861 A1 | 3/2009 |
| WO | 2009/037001 A2 | 3/2009 |
| WO | 2009/052319 A1 | 4/2009 |
| WO | 2009/078992 A1 | 6/2009 |
| WO | 2009/100406 A2 | 8/2009 |
| WO | 2009/109710 A1 | 9/2009 |
| WO | 2009/115267 A2 | 9/2009 |
| WO | 2009/156484 A2 | 12/2009 |
| WO | 2010/006191 A1 | 1/2010 |
| WO | 2010/007046 A2 | 1/2010 |
| WO | 2010/007756 A1 | 1/2010 |
| WO | 2010/008739 A2 | 1/2010 |
| WO | 2010/032147 A2 | 3/2010 |
| WO | 2010/034838 A2 | 4/2010 |
| WO | 2010/046780 A2 | 4/2010 |
| WO | 2010/068863 A2 | 6/2010 |

(56) References Cited

FOREIGN PATENT DOCUMENTS

| | | |
|---|---|---|
| WO | 2010/075376 A2 | 7/2010 |
| WO | 2010/088574 A1 | 8/2010 |
| WO | 2010/108921 A1 | 9/2010 |
| WO | 2010/111527 A1 | 9/2010 |
| WO | 2010/112520 A1 | 10/2010 |
| WO | 2010/127855 A1 | 11/2010 |
| WO | 2010/137350 A1 | 12/2010 |
| WO | 2010/151747 A1 | 12/2010 |
| WO | 2011/008931 A2 | 1/2011 |
| WO | 2011/012661 A1 | 2/2011 |
| WO | 2011/072275 A2 | 6/2011 |
| WO | 2011/073328 A1 | 6/2011 |
| WO | 2011/082400 A2 | 7/2011 |
| WO | 2011/119869 A1 | 9/2011 |
| WO | 2011/125568 A1 | 10/2011 |
| WO | 2011/133920 A1 | 10/2011 |
| WO | 2011/134925 A1 | 11/2011 |
| WO | 2012/003405 A1 | 1/2012 |
| WO | 2012/004217 A1 | 1/2012 |
| WO | 2012/020131 A2 | 2/2012 |
| WO | 2012/020133 A1 | 2/2012 |
| WO | 2012/024604 A2 | 2/2012 |
| WO | 2012/061337 A1 | 5/2012 |
| WO | 2012/064559 A1 | 5/2012 |
| WO | 2012/074050 A1 | 6/2012 |
| WO | 2012/085650 A1 | 6/2012 |
| WO | 2012/085789 A1 | 6/2012 |
| WO | 2012/101062 A1 | 8/2012 |
| WO | 2012/117097 A1 | 9/2012 |
| WO | 2012/123745 A1 | 9/2012 |
| WO | 2012/127385 A1 | 9/2012 |
| WO | 2012/147890 A1 | 11/2012 |
| WO | 2012/149540 A1 | 11/2012 |
| WO | 2012/152915 A1 | 11/2012 |
| WO | 2012/154880 A1 | 11/2012 |
| WO | 2012/156918 A1 | 11/2012 |
| WO | 2012/156919 A1 | 11/2012 |
| WO | 2012/156920 A1 | 11/2012 |
| WO | 2012/166951 A1 | 12/2012 |
| WO | 2013/013815 A1 | 1/2013 |
| WO | 2013/013817 A1 | 1/2013 |
| WO | 2013/017480 A1 | 2/2013 |
| WO | 2013/024004 A1 | 2/2013 |
| WO | 2013/033068 A1 | 3/2013 |
| WO | 2013/041602 A1 | 3/2013 |
| WO | 2013/055984 A1 | 4/2013 |
| WO | 2013/059648 A1 | 4/2013 |
| WO | 2013/064884 A1 | 5/2013 |
| WO | 2013/152198 A1 | 10/2013 |
| WO | 2013/152727 A1 | 10/2013 |
| WO | 2013/163404 A1 | 10/2013 |
| WO | 2013/178816 A1 | 12/2013 |
| WO | 2013/180193 A1 | 12/2013 |
| WO | 2013/188813 A2 | 12/2013 |
| WO | 2014/000418 A1 | 1/2014 |
| WO | 2014/005125 A2 | 1/2014 |
| WO | 2014/012511 A1 | 1/2014 |
| WO | 2014/015167 A2 | 1/2014 |
| WO | 2014/025808 A1 | 2/2014 |
| WO | 2014/031928 A2 | 2/2014 |
| WO | 2014/047111 A1 | 3/2014 |
| WO | 2014/055955 A1 | 4/2014 |
| WO | 2014/056620 A1 | 4/2014 |
| WO | 2014/074906 A1 | 5/2014 |
| WO | 2014/081299 A1 | 5/2014 |
| WO | 2014/081300 A1 | 5/2014 |
| WO | 2014/081301 A1 | 5/2014 |
| WO | 2014/081303 A1 | 5/2014 |
| WO | 2014/089112 A1 | 6/2014 |
| WO | 2014/144169 A1 | 9/2014 |
| WO | 2014/146995 A1 | 9/2014 |
| WO | 2014/149164 A1 | 9/2014 |
| WO | 2014/151936 A1 | 9/2014 |
| WO | 2014/153208 A1 | 9/2014 |
| WO | 2014/164704 A2 | 10/2014 |
| WO | 2014/181287 A1 | 11/2014 |
| WO | 2014/187297 A1 | 11/2014 |
| WO | 2014/187298 A1 | 11/2014 |
| WO | 2014/190199 A1 | 11/2014 |
| WO | 2014/194270 A1 | 12/2014 |
| WO | 2015/031725 A1 | 3/2015 |
| WO | 2015/035059 A1 | 3/2015 |
| WO | 2015/051043 A1 | 4/2015 |
| WO | 2015/051458 A1 | 4/2015 |
| WO | 2015/061247 A2 | 4/2015 |
| WO | 2015/077246 A1 | 5/2015 |
| WO | 2015/110999 A1 | 7/2015 |
| WO | 2015/120800 A1 | 8/2015 |
| WO | 2015/140572 A1 | 9/2015 |
| WO | 2015/142903 A2 | 9/2015 |
| WO | 2015/157057 A1 | 10/2015 |
| WO | 2015/170218 A1 | 11/2015 |
| WO | 2016/020307 A1 | 2/2016 |
| WO | 2016/042341 A1 | 3/2016 |
| WO | 2016/057779 A2 | 4/2016 |
| WO | 2016/058544 A1 | 4/2016 |
| WO | 2016/061527 A1 | 4/2016 |
| WO | 2016/100711 A1 | 6/2016 |
| WO | 2016/133838 A1 | 8/2016 |
| WO | 2016/173557 A1 | 11/2016 |
| WO | 2016/176657 A1 | 11/2016 |
| WO | 2016/183266 A1 | 11/2016 |
| WO | 2017/007755 A1 | 1/2017 |
| WO | 2017/007756 A1 | 1/2017 |
| WO | 2017/027984 A1 | 2/2017 |
| WO | 2017/044889 A1 | 3/2017 |
| WO | 2017/046133 A1 | 3/2017 |
| WO | 2017/075694 A1 | 5/2017 |
| WO | 2017/106818 A1 | 6/2017 |
| WO | 2017/146116 A1 | 8/2017 |
| WO | 2017/156265 A1 | 9/2017 |

OTHER PUBLICATIONS

Gura et al. (Science 1997, Nov. 7, 278) (Year: 1997).*
Neidle, Stephen, ed., Cancer Drug Design and Discovery:(Elsevier/Academic Press, 2008) (Year: 2008).*
Cecil Textbook of Medicine, 20th Edition, vol. 1, 1996 (Year: 1996).*
Grohol, https://psychcentral.com/disorders/ pp. 6-8, 2019 (Year: 2019).*
CDC and Fungal diseases, p. 1, 2011 (Year: 2011).*
Stevens (Continuum of Care, UNM School of Medicine, 2000 (Year: 2000).*
Dorostkar (Acta Neuropath 2015, 130, 1-19) (Year: 2015).*
CAS Registry No. 1072874-82-8. Entered STN: Nov. 14, 2008, 1 page.
Wagner et al., Kinetically Selective Inhibitors of Histone Deacetylase 2 (HDAC2) as Cognition Enhancers. Chem Sci. Jan. 1, 2015;6(1):804-815.
Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8.
Copending U.S. Appl. No. 15/741,657, filed Jan. 3, 2018.
Copending U.S. Appl. No. 15/741,609, filed Jan. 3, 2018.
Copending U.S. Appl. No. 15/867,982, filed Jan. 11, 2018.
Abel et al., pigenetic targets of HDAC inhibition in neurodegenerative and psychiatric disorders. Curr Opin Pharmacol. Feb. 2008;8(1):57-64.
Bowers et al., The Class I HDAC inhibitor RGFP963 enhances consolidation of cued fear extinction. Learn Mem. Mar. 16, 2015;22(4):225-31.
Choong et al., A novel histone deacetylase 1 and 2 isoform-specific inhibitor alleviates experimental Parkinson's Disease. Neurobiology of Aging. DOI: 10.1016/j.neurobiolaging.2015.10.001, 54 pages, Oct. 2, 2015.
Faraco et al., The therapeutic potential of HDAC inhibitors in the treatment of multiple sclerosis. Mol Med. May-Jun. 2011;17(5-6):442-7.

(56) References Cited

OTHER PUBLICATIONS

Fischer et al., Recovery of learning and memory is associated with chromatin remodelling. Nature. May 10, 2007;447(7141):178-82.

Graff et al., An epigenetic blockade of cognitive functions in the neurodegenerating brain. Nature. Feb. 29, 2012;483(7388):222-6.

Guan et al., HDAC2 negatively regulates memory formation and synaptic plasticity. Nature. May 7, 2009;459(7243):55-60.

Herman et al., Histone deacetylase inhibitors reverse gene silencing in Friedreich's ataxia. Nat Chem Biol. Oct. 2006;2(10):551-8.

Levenson et al., Regulation of histone acetylation during memory formation in the hippocampus. J Biol Chem. Sep. 24, 2004;279(39):40545-59.

Masliah et al., Altered expression of synaptic proteins occurs early during progression of Alzheimer's disease. Neurology. Jan. 9, 2001;56(1):127-9.

Mielcarek et al., SAHA decreases HDAC 2 and 4 levels in vivo and improves molecular phenotypes in the R6/2 mouse model of Huntington's disease. PLoS One. 2011;6(11):e27746, 10 pages.

Qin et al., Social deficits in Shank3-deficient mouse models of autism are rescued by histone deacetylase (HDAC) inhibition. Nat Neurosci. Apr. 2018;21(4):564-575.

Schulz-Schaeffer, The synaptic pathology of alpha-synuclein aggregation in dementia with Lewy bodies, Parkinson's disease and Parkinson's disease dementia. Acta Neuropathol. Aug. 2010;120(2):131-43.

She et al., Selectivity and Kinetic Requirements of HDAC Inhibitors as Progranulin Enhancers for Treating Frontotemporal Dementia. Cell Chem Biol. Jul. 20, 2017;24(7):892-906.e5.

Sprow et al., Histone acetylation in the nucleus accumbens shell modulates ethanol-induced locomotor activity in DBA/2J mice. Alcohol Clin Exp Res. Sep. 2014;38(9):2377-86.

Tan et al., Upregulation of histone deacetylase 2 in laser capture nigral microglia in Parkinson's disease. Neurobiol Aging. Aug. 2018; 8 pages, pre-publication version.

Xu et al., Dendritic spine dysgenesis in Rett syndrome. Front Neuroanat. Sep. 10, 2014;8:97. 8 pages.

\* cited by examiner

BICYCLIC INHIBITORS OF HISTONE DEACETYLASE

RELATED APPLICATIONS

This application is a continuation of U.S. application Ser. No. 15/867,982, filed on Jan. 11, 2018, which claims priority to U.S. Provisional Application No. 62/445,022 filed Jan. 11, 2017 and U.S. Provisional Application No. 62/555,298 filed Sep. 7, 2017. Each of the aforementioned applications are incorporated herein by reference.

STATEMENT REGARDING FEDERALLY SPONSORED RESEARCH AND DEVELOPMENT

This invention was made with government support under Small Business Innovation Research (SBIR) grant 1R43AG048651-01A1 awarded by the National Institute of Health (NIH). The government has certain rights in the invention.

BACKGROUND

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs. Marks, P., Rifkind, R. A., Richon, V. M., Breslow, R., Miller, T., Kelly, W. K. Histone deacetylases and cancer: causes and therapies. Nat Rev Cancer, 1, 194-202, (2001); and Marks, P. A., Richon, V. M., Miller, T., Kelly, W. K. Histone deacetylase inhibitors. Adv Cancer Res, 91, 137-168, (2004). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. Langley, B., Gensert, J. M., Beal, M. F., Ratan, R. R. Remodeling chromatin and stress resistance in the central nervous system: histone deacetylase inhibitors as novel and broadly effective neuroprotective agents. Curr Drug Targets CNS Neurol Disord, 4, 41-50, (2005). A recent review has summarized the evidence that aberrant histone acetyltransferase (HAT) and histone deacetylases (HDAC) activity may represent a common underlying mechanism contributing to neurodegeneration. Moreover, using a mouse model of depression, Nestler has recently highlighted the therapeutic potential of histone deacetylation inhibitors (HDAC5) in depression. Tsankova, N. M., Berton, O., Renthal, W., Kumar, A., Neve, R. L., Nestler, E. J. Sustained hippocampal chromatin regulation in a mouse model of depression and antidepressant action. Nat Neurosci, 9, 519-525, (2006).

There are 18 known human histone deacetylases, grouped into four classes based on the structure of their accessory domains. Class I includes HDAC1, HDAC2, HDAC3, and HDAC8 and has homology to yeast Rpd3. HDAC4, HDAC5, HDAC7, and HDAC9 belong to class IIa and have homology to yeast Hda1. HDAC6 and HDAC10 contain two catalytic sites and are classified as class IIb. Class III (the sirtuins) includes SIRT1, SIRT2, SIRT3, SIRT4, SIRT5, SIRT6, and SIRT7. HDAC11 is another recently identified member of the HDAC family and has conserved residues in its catalytic center that are shared by both class I and class II deacetylases and is sometimes placed in class IV.

HDACs have been shown to be powerful negative regulators of long-term memory processes. Nonspecific HDAC inhibitors enhance synaptic plasticity as well as long-term memory (Levenson et al., 2004, J. Biol. Chem. 279:40545-40559; Lattal et al., 2007, Behav Neurosci 121:1125-1131; Vecsey et al., 2007, J. Neurosci 27:6128; Bredy, 2008, Learn Mem 15:460-467; Guan et al., 2009, Nature 459:55-60; Malvaez et al., 2010, Biol. Psychiatry 67:36-43; Roozendaal et al., 2010, J. Neurosci. 30:5037-5046). For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition have considerable therapeutic potential for many memory and cognitive disorders.

The role of individual HDACs in long-term memory has been explored in two recent studies. Kilgore et al. 2010, Neuropsychopharmacology 35:870-880 revealed that non-specific HDAC inhibitors, such as sodium butyrate, inhibit class I HDACs (HDAC1, HDAC2, HDAC3, HDAC8) with little effect on the class IIa HDAC family members (HDAC4, HDAC5, HDAC7, HDAC9). This suggests that inhibition of class I HDACs may be critical for the enhancement of cognition observed in many studies. Indeed, forebrain and neuron specific overexpression of HDAC2, but not HDAC1, decreased dendritic spine density, synaptic density, synaptic plasticity and memory formation. (Guan et al., 2009, Nature, 459:55-60). In contrast, HDAC2 knockout mice exhibited increased synaptic density, increased synaptic plasticity and increased dendritic density in neurons. These HDAC2 deficient mice also exhibited enhanced learning and memory in a battery of learning behavioral paradigms. This work demonstrates that HDAC2 is a key regulator of synaptogenesis and synaptic plasticity. Additionally, Guan et al. showed that chronic treatment of mice with SAHA (an HDAC 1, 2, 3, 6, 8 inhibitor) reproduced the effects seen in the HDAC2 deficient mice and rescued the cognitive impairment in the HDAC2 overexpressing mice.

The inhibition of HDAC2 (selectively or in combination with inhibition of other class I HDACs; as the primary target, or as part of a complex with other proteins) is an attractive therapeutic target. Selective inhibition might be achieved by targeting specific HDAC isoforms such as HDAC2, in isolation, or as part of a functional multi-protein complex. Such inhibition has the potential for enhancing cognition and facilitating the learning process through increasing synaptic and dendritic density in neuronal cell populations. In addition, inhibition of specific HDACs, such as HDAC2, may also be therapeutically useful in treating a wide variety of other diseases and disorders.

SUMMARY

Disclosed are compounds and pharmaceutically acceptable salts thereof, and pharmaceutical compositions, which are useful in the treatment of conditions associated with the activity of HDAC (e.g., HDAC2). (See e.g., Tables 1 and 2).

The disclosed compounds provide an advantage in hematological safety and overall balance of potency, ADME and PK profiles when compared to prior inhibitors. For example, the mere replacement of hydrogen for methyl between Comparator E and Compound 2 leads to a dramatic decrease in CYP2D6 inhibition. See e.g., Table 2. Also, this replacement provides distinct PK benefits over the unsubstituted pyrimidine analog, displaying a longer half-life, lower clearance, higher bioavailability, and a >5-fold higher brain exposure. See e.g., Table 3. Similarly, the addition of one additional ortho-fluorine atom realized a significant safety benefit in both the erythroid and myeloid progenitor cell lineages for Compound 1 relative to Comparator I. See e.g., Table 5.

The described compounds also produce changes in dendritic spine morphology in the CA1 region of the dorsal hippocampus in wild type mice. See e.g., Table 7. Measures of dendritic spine morphology can identify pharmacological agents which are likely to promote or distort normal cognitive function and protect against or exacerbate cognitive impairments.

Conditions which are treatable by the disclosed compounds include, but are not limited to, neurological disorders, memory or cognitive function disorders or impairments, extinction learning disorders, fungal diseases or infections, inflammatory diseases, hematological diseases, neoplastic diseases, psychiatric disorders, and memory loss.

DETAILED DESCRIPTION

1. Compounds

Provided herein is a compound of the formula:

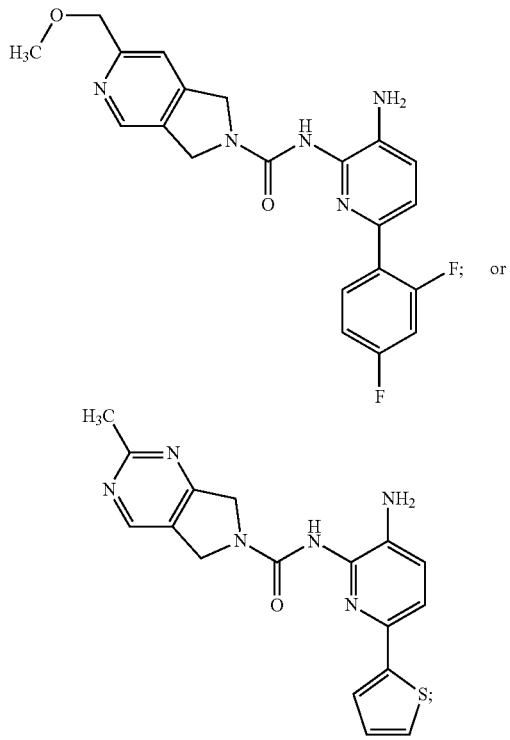

or a pharmaceutically acceptable salt thereof.

2. Definitions

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Pharmaceutically acceptable salts as well as the neutral forms of the compounds described herein are included. For use in medicines, the salts of the compounds refer to non-toxic "pharmaceutically acceptable salts." Pharmaceutically acceptable salt forms include pharmaceutically acceptable acidic/anionic or basic/cationic salts. Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts. Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" or "therapeutically effective amount" includes an amount of a compound described herein that will elicit a biological or medical response of a subject.

3. Uses, Formulation and Administration

In some embodiments, compounds and compositions described herein are useful in treating conditions associated with the activity of HDAC. Such conditions include for example, those described below.

Recent reports have detailed the importance of histone acetylation in central nervous system ("CNS") functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525; Bousiges et al., 2013, PLoS ONE 8(3), e57816). Thus, in one aspect, the provided compounds and compositions may be useful in treating a neurological disorder. Examples of neurological disorders include: (i) chronic neurodegenerative diseases such as fronto-temporal lobar degeneration (frontotemporal dementia, FTD), FTD-GRN, familial and sporadic amyotrophic lateral sclerosis (FALS and ALS, respectively), familial and sporadic Parkinson's disease, Parkinson's disease dementia, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, striatonigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurological disorders affecting sensory neurons include Friedreich's ataxia, diabetes, peripheral neuropathy, and retinal neuronal degeneration. Other neurological disorders include nerve injury or trauma associated with spinal cord injury. Neurological disorders of limbic and cortical systems include cerebral amyloidosis, Pick's atrophy, and Rett syndrome. In another aspect, neurological disorders include disorders of mood, such as affective disorders and anxiety; disorders of social behavior, such as character defects and personality disorders; disorders of learning, memory, and intelligence, such as mental retardation and dementia. Thus, in one aspect the disclosed compounds and compositions may be useful in treating schizophrenia, delirium, attention deficit hyperactivity disorder (ADHD), schizoaffective disorder, Alzheimer's disease, vascular dementia, Rubinstein-Taybi syndrome, depression, mania, attention deficit disorders, drug addiction, dementia, dementia including BPSD manifestations, agitation, apathy, anxiety, psychoses, personality disorders, bipolar disorders, unipolar affective disorder, obsessive-compulsive disorders, eating disorders, post-traumatic stress disorders, irritability, adolescent conduct disorder and dis-inhibition. They may also be useful for spontaneous, toxic, neoplastic, post-traumatic and post-infectious tinnitus and smelling impairment.

Transcription is thought to be a key step for long-term memory formation (Alberini, 2009, Physiol. Rev. 89, 121-145). Transcription is promoted by specific chromatin modifications, such as histone acetylation, which modulate histone—DNA interactions (Kouzarides, 2007, Cell, 128:693-705), as well as transcription factor-DNA interactions. Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing, although treatment with HDAC inhibitors can result in both upregulation and downregulation of the expression levels of specific genes. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467). Thus, in one aspect, the provided compounds and compositions may be useful for promoting cognitive function and enhancing learning and memory formation.

The compounds and compositions described herein may also be used for treating fungal diseases or infections.

In another aspect, the compounds and compositions described herein may be used for treating inflammatory diseases such as stroke, rheumatoid arthritis, lupus erythematosus, ulcerative colitis and traumatic brain injuries (Leoni et al., PNAS, 99(5); 2995-3000(2002); Suuronen et al. J. Neurochem. 87; 407-416 (2003) and Drug Discovery Today, 10: 197-204 (2005).

In yet another aspect, the compounds and compositions described herein may be used for treating a cancer caused by the proliferation of neoplastic cells. Such cancers include e.g., solid tumors, neoplasms, carcinomas, sarcomas, leukemias, lymphomas and the like. In one aspect, cancers that may be treated by the compounds and compositions described herein include, but are not limited to: cardiac cancer, lung cancer, gastrointestinal cancer, genitourinary tract cancer, liver cancer, nervous system cancer, gynecological cancer, hematologic cancer, skin cancer, and adrenal gland cancer. In one aspect, the compounds and compositions described herein are useful in treating cardiac cancers selected from sarcoma (angiosarcoma, fibrosarcoma, rhabdomyosarcoma, liposarcoma), myxoma, rhabdomyoma, fibroma, lipoma and teratoma. In another aspect, the compounds and compositions described herein are useful in treating a lung cancer selected from bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma. In one aspect, the compounds and compositions described herein are useful in treating a gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), and large bowel (adenocarcinoma, tubular adenoma, villous adenoma, hamartoma, leiomyoma). In one aspect, the compounds and compositions described herein are useful in treating a genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In one aspect, the compounds and compositions described herein are useful in treating a liver cancer selected from hepatoma (hepatocellular carcinoma), cholangiocarcinoma, hepatoblastoma, angiosarcoma, hepatocellular adenoma, and hemangioma.

In some embodiments, the compounds described herein relate to treating, a bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors.

In one aspect, the compounds and compositions described herein are useful in treating a nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In one aspect, the compounds and compositions described herein are useful in treating a gynecological cancer selected from uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In one aspect, the compounds and compositions described herein are useful in treating a skin cancer selected from malignant melanoma, basal cell carcinoma, squamous cell carcinoma, Karposi's sarcoma, moles dysplastic nevi, lipoma, angioma, dermatofibroma, keloids, and psoriasis.

In one aspect, the compounds and compositions described herein are useful in treating an adrenal gland cancer selected from neuroblastoma.

In one aspect, the compounds and compositions described herein are useful in treating cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In one aspect, the compounds and compositions described herein are useful in treating a condition in a subject selected from a neurological disorder, memory or cognitive function disorder or impairment, extinction learning disorder, fungal disease or infection, inflammatory disease, hematological disease, psychiatric disorders, and neoplastic disease. In another aspect, the compounds and compositions described herein are useful in treating a condition selected from a) a cognitive function disorder or impairment associated with Alzheimer's disease, Huntington's disease, seizure induced memory loss, schizophrenia, Rubinstein Taybi syndrome, Rett Syndrome, Fragile X, Lewy body dementia, vascular dementia, fronto-temporal lobar degeneration (frontotemporal dementia, FTD), FTD-GRN, ADHD, dyslexia, bipolar disorder and social, cognitive and learning disorders associated with autism, traumatic head injury, attention deficit disorder, anxiety disorder, conditioned fear response, panic disorder, obsessive compulsive disorder, posttraumatic stress disorder (PTSD), phobia, social anxiety disorder, substance dependence recovery, Age Associated Memory Impairment (AAMI), Age Related Cognitive Decline (ARCD), ataxia, or Parkinson's disease; b) a hematological disease selected from acute myeloid leukemia, acute promyelocytic leukemia, acute lymphoblastic leukemia, chronic myelogenous leukemia, myelodysplastic syndromes, and sickle cell anemia; c) a neoplastic disease; and d) an extinction learning disorder selected from fear extinction and post-traumatic stress disorder. In one aspect, the condition treated by the compounds and compositions described herein is Alzheimer's disease, Huntington's disease, frontotemporal dementia, Freidreich's ataxia, post-traumatic stress disorder (PTSD), Parkinson's disease, depression, or substance dependence recovery.

In one aspect, the present disclosure provides a method of treating a condition described herein comprising administering to a subject an effective amount of a compound, or pharmaceutically acceptable salt described herein, or a composition thereof.

Also provided is the use of one or more of the compounds, or pharmaceutically acceptable salts thereof described herein, or a provided composition, for treating a condition described herein.

Also provided is the use of one or more of the compounds, or pharmaceutically acceptable salts thereof described herein for the manufacture of a medicament for treating a condition described herein.

Subjects may also be selected to be suffering from one or more of the described conditions before treatment with one or more of the described compounds, or pharmaceutically acceptable salts or compositions commences.

The present disclosure also provides pharmaceutically acceptable compositions comprising a compound described herein, or a pharmaceutically acceptable salt thereof; and a pharmaceutically acceptable carrier. These compositions can be used to treat one or more of the conditions described above.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a compound are included herein.

The amount of provided compounds that may be combined with carrier materials to produce a composition in a single dosage form will vary depending upon the patient to be treated and the particular mode of administration. In some embodiments, provided compositions may be formulated so that a dosage of between 0.01-100 mg/kg body weight/day of the provided compound, such as e.g., 0.1-100 mg/kg body weight/day, can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

EXEMPLIFICATION

Spots were visualized by UV light (254 and 365 nm). Purification by column and flash chromatography was carried out using silica gel (200-300 mesh). Solvent systems are reported as the ratio of solvents.

NMR spectra were recorded on a Bruker 400 (400 MHz) spectrometer. $^1$H chemical shifts are reported in δ values in ppm with tetramethylsilane (TMS, =0.00 ppm) as the internal standard. See, e.g., the data provided in Table 1.

LCMS spectra were obtained on an Agilent 1200 series 6110 or 6120 mass spectrometer with ESI (+) ionization mode. See, e.g., the data provided in Table 1.

Example 1

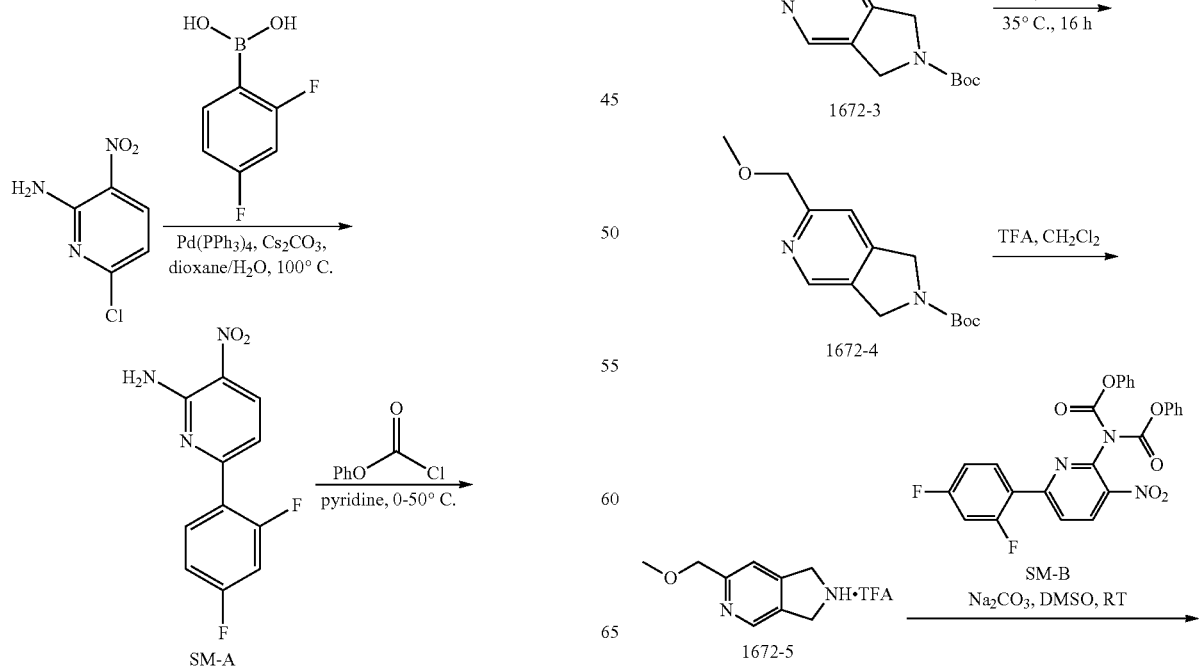

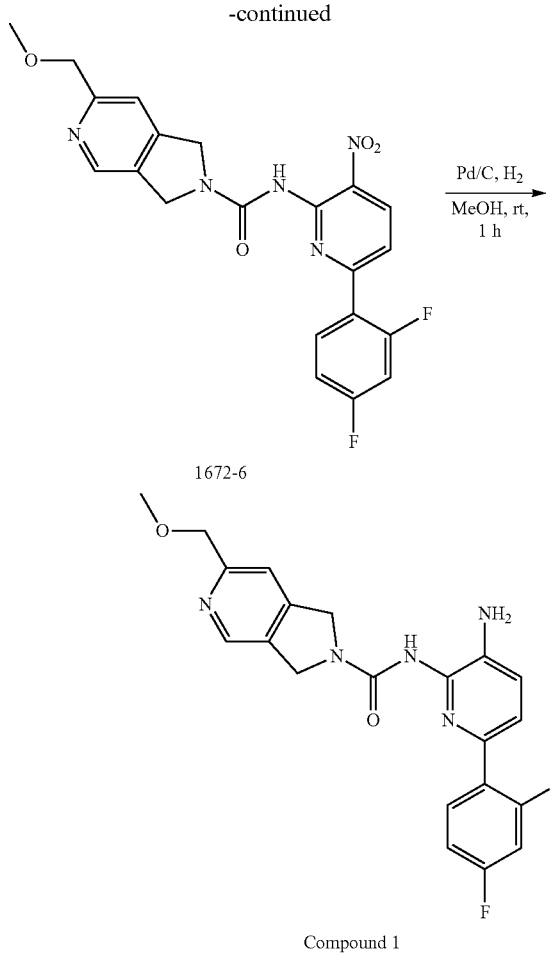

1672-6

Compound 1

Synthesis of SM-A.

A mixture of 6-chloro-3-nitropyridin-2-amine (4.58 g, 26.4 mmol), 2,4-difluorophenylboronic acid (5.00 g, 31.7 mmol) and Cs$_2$CO$_3$ (25.73 g, 79.2 mmol) in dioxane/H$_2$O (100 mL/10 mL) was added Pd(PPh$_3$)$_4$ (1.10 g, 0.95 mmol) under N$_2$ atmosphere. The mixture was stirred at 100° C. for 2 h and then concentrated in vacuo. The residue was dissolved with EtOAc (200 mL) and the solution was washed with brine (100 mL×3). The organic layer was dried over anhydrous Na$_2$SO$_4$ and then concentrated in vacuo. The residue was purified by column chromatography on silica gel (PE:EtOAc=7:1~5:1) to give SM-A (4.0 g, 61%) as a yellow solid. MS 252.1 [M+H]$^+$.

Synthesis of SM-B.

To a stirring solution of SM-A (4.0 g, 15.94 mmol) in pyridine (60 mL) was added phenyl carbonochloridate (7.50 g, 47.81 mmol) dropwise at 0° C. After the addition was completed, the mixture was stirred at 50° C. for 4 h. The mixture was concentrated in vacuo. The residue was purified by column chromatography on silica gel (PE:DCM=3:2~1:1) to give SM-B (7.1 g, 91%) as a yellow solid. MS 492.1 [M+H]$^+$.

Synthesis of 1672-1.

To a solution of prop-2-yn-1-amine (5.0 g, 90.9 mmol) and Et$_3$N (18.4 g, 181.8 mmol) in DCM (100 mL) was added (Boc)$_2$O (23.8 g, 109.1 mmol) dropwise while cooling the reaction mixture with an ice bath. The resulting mixture was removed from the ice bath once the addition was completed, and was then stirred at room temperature for 16 h. When the reaction was complete, the mixture was diluted with DCM (200 mL), washed with brine (100 mL×3), and the organic layer was then dried over Na$_2$SO$_4$ and then concentrated in vacuo. The residue was purified by column chromatography on silica gel (PE:EtOAc=100:1~10:1) to give 1672-1 (10 g, 71%) as a colorless oil. MS 178.3 [M+23]$^+$, 100.3 [M−56]$^+$.

Synthesis of 1672-2.

To a solution of 1672-1 (10 g, 64.5 mmol) in DMF (200 mL) was added NaH (60% in mineral oil) (2.84 g, 71 mmol) slowly under ice bath. The resulting mixture was stirred at room temperature for 1 h, whereupon 3-bromoprop-1-yne (9.2 g, 77.4 mmol) was added into above mixture, and the reaction mixture was then stirred at room temperature for 2 h. The mixture was quenched with water (500 mL) and then extracted with t-BuOMe (250 mL×3). The combined organic layers were washed with brine (200 mL×3), dried over anhydrous Na$_2$SO$_4$ and then concentrated in vacuo. The residue was purified by column chromatography on silica gel (PE:EtOAc=100:1~10:1) to give 1672-2 (12 g, 96%) as a yellow oil. MS 138.1 [M−56]$^+$.

Synthesis of 1672-3.

To a solution of 2-chloroacetonitrile (3.13 g, 41.4 mmol) and [Cp*RuCl(cod)] (394 mg, 1.0 mmol) in DCE (40 mL) was added a solution of 1672-2 (4.0 g, 20.7 mmol) in DCE (80 mL) dropwise over 30 min under an N$_2$ atmosphere. The resulting mixture was stirred at 40° C. for 16 h. The solvent was removed in vacuo, and the residue was purified by column chromatography on silica gel (PE:EtOAc=10:1~2:1) to give 1672-3 (2.1 g, 22%) as a khaki solid. MS 269.3 [M+H]$^+$.

Synthesis of 1672-4.

To a solution of MeOH (30 mL) was added NaH (60% in mineral oil) (940 mg, 23.5 mmol) at ice bath and stirred for 30 min. Then 1672-C (2.1 g, 7.8 mmol) was added into above mixture and stirred at 35° C. for 16 h. The mixture was quenched with water (30 mL), extracted with DCM (10 mL×3). The combined organic layers were washed with brine (10 mL×3), dried over anhydrous Na$_2$SO$_4$ and then concentrated in vacuo. The residue was purified by column chromatography on silica gel (PE:EtOAc=100:1~10:1) to give 1672-4 (1.8 g, 94%) as a tan colored solid. MS 265.1 [M+H]$^+$.

Synthesis of 1672-5.

To a solution of 1672-4 (120 mg, 0.45 mmol) in DCM (6 mL) cooled in an ice bath was added TFA (2 mL) dropwise. The resulting reaction mixture was stirred at room temperature for 1 h, whereupon the solvent was removed in vacuo to give 1672-5 as a crude product which was taken on to the next step without further purification. MS 165.1 [M+H]$^+$.

Synthesis of 1672-6.

To a mixture of 1672-5 (0.45 mmol, crude product from last step) and SM-B (150 mg, 0.30 mmol) in DMSO (10 mL) was added Na$_2$CO$_3$ (259 mg, 3.44 mmol), and the resulting reaction mixture was stirred at 25° C. for 2 h. The mixture was then diluted with water (30 mL) and extracted with EtOAc (20 mL×3). The combined organic layers were washed with brine (10 mL×3), dried over anhydrous Na$_2$SO$_4$ and then concentrated in vacuo. The residue was purified by column chromatography on silica gel (DCM:MeOH=100:1~30:1) to give 1672-6 (120 mg, 89%) as a yellow solid. MS 442.1 [M+H]$_+$.

Synthesis of Compound 1.

A mixture of 1672-6 (120 mg, 0.27 mmol) and Pd/C (120 mg) in MeOH (10 mL) was stirred at room temperature for 1 h under a H$_2$ atmosphere. Pd/C was then removed by filtration through the celite. The filtrate was concentrated and the residue was purified by Prep-TLC (DCM:

MeOH=15:1) to give Compound 1 (70 mg, 70%) as a yellow solid. MS 412.1 [M+H]+, 434.1 [M+23]+.

Example 2

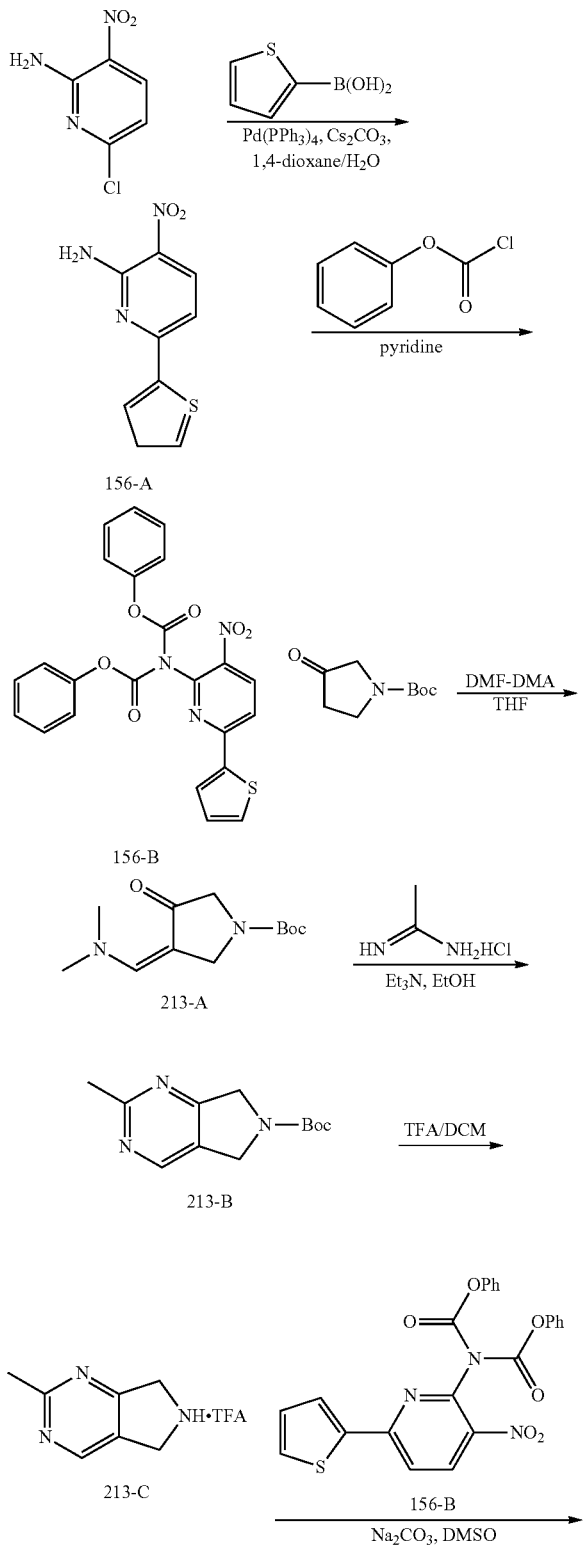

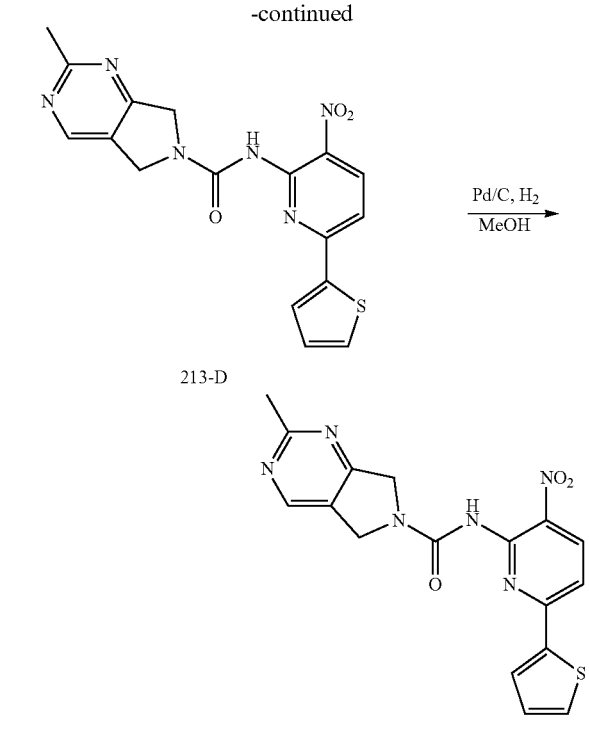

Synthesis of 156-A.

A mixture of 6-chloro-3-nitropyridin-2-amine (10.00 g, 57.6 mmol), thiophen-2-ylboronic acid (8.12 g, 63.4 mmol) and Cs$_2$CO$_3$ (37.56 g, 115.2 mmol) in dioxane/H$_2$O (200 mL/20 mL) was added Pd(PPh$_3$)$_4$ (2.44 g, 2.88 mmol) under an N$_2$ atmosphere. The mixture was stirred at 95° C. for 2 h and then concentrated in vacuo. The residue was dissolved with EtOAc (200 mL) and the solution was washed with brine (100 mL×3). The organic layer was dried over anhydrous Na$_2$SO$_4$ and then concentrated in vacuo. The residue was purified by column chromatography on silica gel (PE:EtOAc=5:1~3:1) to give 156-A (10.0 g, 79%) as a yellow solid Synthesis of 156-B.

To a stirred solution of 156-A (1.30 g, 5.88 mmol) in pyridine (20 mL) was added phenyl carbonochloridate (2.29 g, 14.7 mmol) in dropwise fashion. After the addition was completed, the mixture was heated to 50° C. and stirred for 4 h. The mixture was then concentrated in vacuo, and the residue was purified by column chromatography on silica gel (PE:EtOAc=8:1~3:1) to give 156-B (2.4 g, 89%) as a yellow solid.

Synthesis of 213-A.

A solution of tert-butyl 3-oxopyrrolidine-1-carboxylate (150.0 g, 809.8 mmol) and DMF-DMA (289.5 g, 2.4 mol) in THF (1500 mL) was stirred at 70° C. for 16 h. The solution was concentrated in vacuo to give 213-A as a crude product, which was used directly in the next step without further purification.

Synthesis of 213-B.

To a solution of 213-A (809.8 mmol, crude product from last step) in EtOH (1000 mL) was added Et$_3$N (409.7 g, 4.0 mol) and acetimidamide hydrochloride (306.2 g, 3.2 mol). The resulting solution was stirred at 80° C. for 24 h. After the mixture was cooled to room temperature, the mixture was diluted with water (500 mL) and extracted with DCM (500 mL×3). The combined organic layers were washed with brine (500 mL×3), dried over anhydrous Na$_2$SO$_4$ and then concentrated in vacuo. The residue was purified by column chromatography on silica gel (PE:DCM=10:1~1:2) to give 213-B (105.0 g, 55%) as a brown solid.

Synthesis of 213-C.

To a solution of 213-B (105.0 g, 446.3 mmol) in DCM (1000 mL) was added TFA (333 mL) dropwise. The reaction mixture was stirred at room temperature for 1 h, whereupon the solution was concentrated in vacuo to give 213-C as a crude product which was used directly in the next step.

Synthesis of 213-D.

A mixture of 213-C (325.1 mmol, crude product from last step) and 156-B (75.0 g, 162.5 mmol) in DMSO (750 mL) was stirred at room temperature for 10 min, then Na$_2$CO$_3$ (137.8 g, 1.3 mol) was added, and the reaction mixture was stirred at room temperature for 2 h. The mixture was then diluted with water (1000 mL) and extracted with EtOAc (500 mL×3). The combined organic layers were washed with brine (500 mL×3), dried over anhydrous Na$_2$SO$_4$ and then concentrated in vacuo. The residue was purified by column chromatography on silica gel (PE:EA=10:1~1:2) to give 213-D (44.0 g, 71%) as a yellow solid.

Synthesis of Compound 2.

A mixture of 213-D (44.0 g, 115.1 mmol) and Pd/C (22.0 g) in MeOH (250 mL) and DCM (250 mL) was stirred at room temperature for 1 h under a H$_2$ atmosphere. Pd/C was removed by filtration through Celite. The filtrate was concentrated in vacuo and the residue was purified by column chromatography on silica gel (DCM:MeOH=50:1~15:1) to give Compound 2 (26.0 g, 64%) as a light yellow solid.

TABLE 1

Spectrometric Data for Compounds

| No. | Structure | MS Calc | MS found | $^1$H NMR Data (400 MHz, DMSO-d$_6$) |
|---|---|---|---|---|
| 1 | 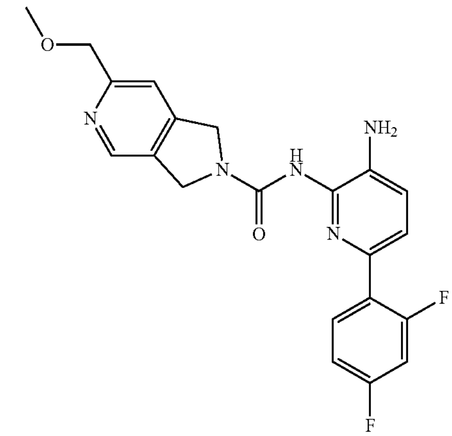 [SMILES: COCc1cc2c(cn1)CN(C(=O)Nc1nc(-c3ccc(F)cc3F)ccc1N)C2] | 411 | 412 | δ 8.58 (s, 1H), 8.53 (s, 1H), 7.97-7.91 (m, 1H), 7.44-7.40 (m, 2H), 7.32-7.26 (m, 1H), 7.18-7.13 (m, 2H), 5.28 (s, 2H), 4.82 (s, 4H), 4.52 (s, 2H), 3.38 (s, 3H). |
| 2 | 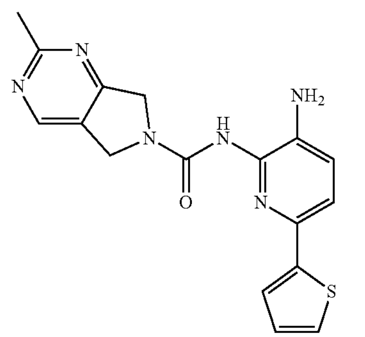 | 352 | 353 | δ 8.70 (s, 1H), 8.60 (s, 1H), 7.53-7.47 (m, 2H), 7.42-7.40 (q, J = 4.0 Hz, 1H), 7.13-7.07 (t, J = 8.0 Hz, 1H), 7.06-7.05 (t, J = 1.2 Hz, 1H), 5.18 (s, 2H), 4.78-4.75 (d, J = 10.4 Hz, 4H), 2.64 (s, 3H). |

General Assay Methods

HDAC2 and HDAC1 Enzymatic Assay

The following describes an assay protocol for measuring the deacetylation of a peptide substrate by the enzymes HDAC2 or HDAC1.

All recombinant human HDACs were purchased from BPS Bioscience. The substrate, FAM-TSRHK(AC)KL-CONH, was synthesized at NanoSyn. Final assay reactions contained 100 mM HEPES (pH 7.5), 50 mM KCl, 0.1% BSA, 0.01% Triton X-100, 1% DMSO, 1 uM substrate and 5 nM HDAC enzyme. Enzyme and compounds were pre-incubated at 25° C. for 5 hours and reactions were initiated by addition of substrate. 10 uL reactions were incubated for 17 hours at 25° C. and terminated by the addition of 40 uL of buffer containing 100 mM HEPES (pH 7.5), 0.1% BSA, 0.01% Triton X-100 and 0.05% SDS. Substrate and product peptides present in each sample were separated electrophoretically using the LabChip 3000 capillary electrophoresis instrument. Change in the relative fluorescence intensity of the substrate and product peaks reflects enzyme activity. Reaction progress was determined as the product to sum ratio (PSR):P/(S+P), where P is the peak height of the product peptide and S is the peak height of the substrate peptide. Reactions were performed in duplicate at 12 concentrations, (3× serial dilutions starting at 30 uM). $IC_{50}$ values were calculated using a 4 Parameter Logistic Model.

HDAC2 Enzymatic Inhibition Assay in SY5Y Cell Lysate with HDAC-Glo2 Substrate

Cell Culture and Inhibitor Treatments

SH-SYSY cells (Sigma) were cultured in Eagle's Modified Essential Medium supplemented with 10% fetal bovine serum and pen/strep. Twenty-four hours prior to compound dosing 20 uL of cells were plated in white 384 well plates at a density of 1,500 cells/well. Compounds were serially diluted in neat DMSO and then diluted 1:100 v/v into media without FBS and mixed. Media was removed from the plated cells and the diluted compounds in serum free media (1% v/v final DMSO) were added and incubated at 37.0 for five hours. Ten uL of HDAC-Glo 2 reagent with 0.1% Triton X-100 was then added, the plate was mixed and allowed to develop at room temperature for 100 minutes. Plates were then read with a Spectramax LMax luminometer employing a 0.4s integration time. Dose response curves were constructed with normalized data where CI-994 at 100 uM was defined as 100% inhibition and DMSO alone as 0% inhibition.

Erythroid and Myeloid CFU Assay

Compounds were tested to evaluate the potential effects on human erythroid and myeloid progenitors using colony forming cell assays. Clonogenic progenitors of human erythroid (CFU-E, BFU-E), granulocyte-monocyte (CFU-GM) and multipotential (CFU-GEMM) lineages were assessed in a semi-solid methylcellulose-based media formulation containing rhIL-3 (10 ng/mL), rhGM-SCF (10 ng/mL), rhSCF (50 ng/mL) and Epo (3 U/mL).

Cells

Normal human bone marrow light density cells derived from normal bone marrow (NorCal Biologics, California) and qualified at ReachBio, were stored in the gaseous phase of liquid nitrogen (−152° C.) until required for the assay. On the day of the experiment, the cells were thawed rapidly, the contents of each vial was diluted in 10 mL of Iscove's modified Dulbecco's medium containing 10% fetal bovine serum (IMDM+10% FBS) and washed by centrifugation (approximately 1200 r.p.m. for 10 minutes, room temperature). The supernatant was discarded and the cell pellets resuspended in a known volume of IMDM+10% FBS. A cell count (3% glacial acetic acid) and viability assessment (trypan blue exclusion test) was performed for the bone marrow sample.

Compounds

On the day of the experiment, the compounds were dissolved in DMSO to a stock concentration of 10 mM. Serial dilutions were prepared from the stock concentration to achieve concentrations of 2 and 0.4 mM. When added to the methylcellulose-based media at 1:1000 (v/v), the final test concentrations of 10, 2 and 0.4 µM were achieved. Additionally, 5-FU was evaluated at 1.0, 0.1 and 0.01 µg/mL.

Method Summary

Clonogenic progenitors of the human erythroid (CFU-E and BFU-E) and myeloid (CFU-GM) lineages were set up in the methylcellulose-based media formulations described above. All compounds were added to the medium to give the final desired concentrations (10, 2 and 0.4 µM). 5-Fluorouracil (Sigma Aldrich) was used as a positive control for progenitor proliferation (inhibition of colony growth) and was introduced to the human bone marrow cultures at 1.0, 0.1, and 0.01 µg/mL. Solvent control cultures (containing no compound but 0.1% DMSO) as well as standard controls (containing no compound and no DMSO) were also initiated.

Human myeloid and erythroid progenitor assays were initiated at $2.0 \times 10^4$ cells per culture. Following 14 days in culture, myeloid and erythroid colonies were assessed microscopically and scored by trained personnel. The colonies were divided into the following categories based on size and morphology: CFU-E, BFU-E, CFU-GM and CFU-GEMM.

Statistical Analyses of CFC Numbers

The mean±one standard deviation of three replicate cultures was calculated for progenitors of each category (CFU-E, BFU-E, etc.). Two-tailed t-tests were performed to assess if there was a difference in the number of colonies generated between solvent control and treated cultures. Due to the potential subjectivity of colony enumeration, a p value of less than 0.01 is deemed significant. To calculate the concentration of 50% inhibition of colony growth ($IC_{50}$) for each compound, a dose response curve was generated plotting the log of the compound concentration versus the percentage of control colony growth using XLfit software (IDBS). The concentration of 50% inhibition of colony growth ($IC_{50}$) was calculated based on the sigmoid curve fit using Dose-Response, One-Site Model formula: $y=A+[(B-A)/(1+((C/x)\hat{}D))]$, where A=the initial value (baseline response), B=maximum response, C=center (drug concentration that provokes a response halfway between A and B) and D=slope of the curve at midpoint. Further, plots and additional dose response curves were generated using GraphPad Prism 7.0.

Morphological Assessment of Colonies

Photographs were taken of representative hematopoietic progenitor-derived colonies from various lineages, illustrating colonies in the presence of the solvent control as well as colonies in the presence of the test compounds.

Erythroid (CFU-E and BFU-E), myeloid (CFU-GM) and multi-potential (CFU-GEMM) colony enumeration was performed by trained personnel. The distribution of colony types as well as general colony and cellular morphology was analyzed. For statistical analysis colony numbers in compound treated cultures were compared to the solvent control cultures. 5-FU was used as a positive control for toxicity in these assays and the inhibitory effects obtained for this compound were exactly as expected. The experiment was used to evaluate the potential effect of test compounds on human erythroid and myeloid progenitor proliferation in a methylcellulose-based medium. The $IC_{50}$ values were calculated from XLfit. Dose response curves for erythroid and myeloid toxicity generated by XLfit. Finally, nonlinear regression curve fitting and $IC_{50}s\pm95\%$ CI, were calculated by Prism 7.0.-GEMM.

CYP Inhibition Assay

Compounds were tested to evaluate their inhibitory potential on CYP2D6 and CYP3A4 (midazolam) using human liver microsomes. Human liver microsomes were obtained from BD Gentest, and each compound was run in duplicate.

The test compounds and reference inhibitors (quinidine for 2D6, ketoconazole for 3A4) were plated in a 96-well plate by transferring 8 µL of 10 mM stock solutions of compound in DMSO to 12 µL of acetonitrile. Individual inhibitor spiking solutions were prepared for CYP2D6 and CYP3A4 (8 µL of DMSO stock added to 12 µL of acetonitrile). Next added 400 µL of 0.2 mg/mL HLM to the assay wells and then added 2 µL of 400×test compound into the designated wells on ice. Next, added 200 µL of 0.2 mg/mL HLM to the assay wells and then added 1 µL of reference inhibitor solutions into the designated wells. The following solutions were added (in duplicate) to a 96-well assay plate on ice: The test compounds and reference inhibitors (quinidine for 2D6, ketoconazole for 3A4) were tested using the following experimental procedure:

1. Prepare test compound and reference inhibitors (400×) in a 96-well plate:
  1.1. Transfer 8 µL of 10 mM test compounds to 12 µL of ACN.
  1.2. Prepare individual inhibitor spiking solution for CYP3A4, CYP2D6: 8 µL of DMSO stock to 12 µL of ACN.
2. Prepare 4×NADPH cofactor (66.7 mg NADPH in 10 mL 0.1 M K-buffer, pH 7.4)
3. Prepare 4×substrate (2 mL for each isoform) as indicated in the table below (add HLM where required on ice).
4. Prepare 0.2 mg/mL HLM solution (10 µL of 20 mg/mL to 990 µL of 0.1 M K-buffer) on ice.
5. Add 400 µL of 0.2 mg/mL HLM to the assay wells and then add 2 µL of 400×test compound into the designated wells on ice.
6. Add 200 µL of 0.2 mg/mL HLM to the assay wells and then add 1 µL of reference inhibitor solution into the designated wells on ice.
7. Add following solutions (in duplicate) in a 96-well assay plate on ice:
  7.1. Add 30 µL of 2×test compound and reference compound in 0.2 mg/mL HLM solution;
  7.2. Add 15 µL of 4×substrate solution.
8. Pre-incubate the 96-well assay plate and NADPH solution at 37° C. for 5 minutes.
9. Add 15 µL of pre-warmed 8 mM NADPH solution to into the assay plates to initiate the reaction
10. Incubate the assay plate at 37° C. 5 min for 3A4, 10 min for 2D6.
11. Stop the reaction by adding 120 µL of ACN containing Internal Standard. For CYP3A4, the internal standard is 1'OH-midazolam-$D_4$ (10 µM solution diluted to a final concentration of 0.1 µM by adding 100 µL internal standard stock to 10 mL ACN). For CYP2D6, the internal standard is 1-OH-Bufuralol-maleate-[$D_9$] (49 µM solution diluted to a final concentration of 0.1 µM by adding 20 µL internal standard stock to 10 mL ACN).
12. After quenching, shake the plates at the vibrator (IKA, MTS 2/4) for 10 min (600 rpm/min) and then centrifuge at 5594 g for 15 min (Thermo Multifuge×3R).
13. Transfer 50 µL of the supernatant from each well into a 96-well sample plate containing 50 µL of ultra pure water (Millipore, ZMQS50F01) for LC/MS analysis.

The assessment on CYP isoform inhibition is as follows based on the assay results: if percentage of CYP inhibition is higher than 50%, indicates potent inhibition; if percentage of CYP inhibition is between 30-50%, indicates slight inhibition; if percentage of CYP inhibition is less than 30%, indicates slight or no inhibition. If the percentage of CYP inhibition is less than −30%, this indicates the compound may have some kind of activation of this isoform.

Aqueous Kinetic Solubility Measurement

Compounds were evaluated for their kinetic solubility in buffer or water. Aliquots of 8 µL of reference and test compound stock solutions (10 mM in DMSO) were added into 792 µL of 100 mM phosphate buffer (0.1 M $NaPO_4$, pH 7.4). Final DMSO concentration is 1%. The sample tubes were shaken for 1 hour (1000 rpm) at room temperature. A calibration curve was prepared using 300 µM spiking solution (SS) in MeOH/ACN(4:1) (SS=add 6 µL 10 mM compoud in 194 uL MeOH/ACN(4:1)). Samples were centrifuged for 10 mM (12000 rpm) to precipitate undissolved particles, and the supernatants were transferred to a new tube or plate. Supernatants were diluted 10 times and 100 times with 100 mM buffer. Samples were then prepared for analysis by LC-MS/MS (Add 5 µL of compound samples (not diluted, 10 times diluted and 100 times diluted) and standard curve samples to 95 µL of ACN containing internal standard. Internal standards used are Propranolol, Ketoconazole, and Tamoxifen.

Assessment of Brain and Plasma Exposure for Compounds Following Intravenous (IV) and Oral (PO) Administration to Mice Compounds were dosed in mice at either 10 mg/kg or 30 mg/kg PO, and were dosed at 1 mg/kg IV. Three animals for collection at each time point for plasma via bleeding at 0.25, 0.5, 1, 4, 12 and 24 h. Terminal bleeding for plasma and sampling for brain at 0.25, 0.5, 1, 4, 12 and 24 h (also three animals per brain exposure time point group). Total of six time points for plasma and six time points for brain.

Sample Collection:

Plasma: The animal was restrained manually at the designated time points, approximately 150 µL blood/time point was collected into $K_2$EDTA tube via retro orbital puncture or cardiac puncture under anesthesia with Isoflurane. The blood sample was centrifuged (2000 g, 4° C., 5 mM) to generate plasma within 30 mM after bleeding.

Brain: At the designated time points, a mid-line incision was made in the animals scalp and the skin was retracted. Using small bone cutters and rongeurs, removed the skull overlying the brain. Removed the brain using a spatula and rinse with cold saline. Placed the brain in screw-top tubes, and then stored the tubes under −70° C. until analysis.

Certain Advantages of Compounds 1 and 2

From a drug discovery standpoint, it is important that compounds have acceptable drug-like profiles across a range of parameters. It is typical to profile compounds not only for in vitro potency, but also in predictive Absorption, Distribution, Excretion and Metabolism (ADME) studies in vitro, and in pharmacokinetic (PK) experiments in vivo. In some cases, compounds are also profiled in predictive in vitro safety studies. Collecting in vitro ADME and safety data, along with PK data, help to identify benefits of certain structural features, and allows the optimization of the structure activity relationship (SAR) to design compounds with optimized drug-like profiles for profiling in vivo. The present compounds not only provide an advantage in hematological safety, but also provide an overall balance of potency, ADME and PK profiles.

Aminoaniline urea compounds such as Comparator A and Comparator B in Table 2 were previously described in WO 2017/007755 and WO 2017/007756 (the contents of each of which are incorporated herein by reference). When screened in an in vitro colony forming unit (CFU) assay in human bone marrow cells, looking at erythroid and myeloid progenitor cells (predictive for neutropenia), and compared to the matched pair aminopyridine urea compound Comparator B, a single atom change in the diaminopyridine urea core of Comparator B leads to a significant improvement in predicted safety in both erythroid and myeloid lineages relative to the urea of the aminoaniline scaffold of Comparator A. See Table 2. Moving forward, when the 4-fluorophenyl group of Comparator B is replaced with a thiophene group (Comparator C), but the pyrrolopyrazine component of the urea is kept the same, a similar improvement in predicted safety profile is achieved relative to the aminoaniline urea Comparator A. This evidences that ureas of diaminopyridine compounds with identical pyrrolidine urea components are safer than the corresponding aminoaniline ureas.

While the pyrrolopyrazine urea compounds, Comparator B and Comparator C, showed good potency in in vitro potency assays, the values from the in vitro CFU assay still require improvement. A myeloid lineage $IC_{50}>5$ μM (roughly corresponding to >30% remaining at 10 μM) predicts low likelihood of clinical neutropenia, so is the target threshold for acceptable safety (References: Pessina et al. *Toxicological Sciences* 2003, 75, 355-367; Clarke et al. *Gen. Eng. & Biotech. News* 2010, 14-15.). It was found that by changing the pyrrolopyrazine to a pyrrolopyrimidine, a significantly improved in vitro safety profile was achieved. Comparing the matched pair Comparator B (pyrrolopyrazine) with Comparator D (pyrrolopyrimidine), a significant improvement in both the CFU erythroid and myeloid progenitor cells is observed. This also holds for the aminopyridine urea matched pairs possessing a thiophene footpocket, Comparator C (pyrrolopyrazine) and Comparator E (pyrrolopyrimidine). Although the pyrimidine brought with it an improved safety profile, both unsubstituted pyrimidine compounds Comparator D and Comparator E showed significant inhibition of CYP2D6 at 10 μM. However, substituting on the pyrimidine ring at the position between the nitrogen atoms, Compound 2 (methyl-substituted pyrrolopyrimidine) showed no significant inhibition of either CYP2D6 or CYP3A4 at 10 μM.

These results evidence that slight chemical modifications such as the walking of a nitrogen atom one position on a ring in Comparators B and D and replacing hydrogen for methyl (Comparators E and Compound 2) produce dramatic increases in safety.

TABLE 2

Comparison of in vitro profile of Compound 2 to multiple comparators.

| Comp. | Structure | HDAC2 SY5Y cell lysate assay IC50 (μM) | HDAC recombinant enzymatic IC50 (μM) HDAC2 | HDAC1 | % CYP inhibition @ 10 μM: 2D6 | 3A4 | CFU % Control remaining @ 10 μM Erythroid | Myeloid |
|---|---|---|---|---|---|---|---|---|
| A | (structure) | 0.369 | 0.142 | 0.027 | 34 | −22 | 0 | 0 |
| B | (structure) | 0.485 | 0.475 | 0.119 | 9 | 1.5 | 9 | 25 |

TABLE 2-continued

Comparison of in vitro profile of Compound 2 to multiple comparators.

| Comp. | Structure | HDAC2 SY5Y cell lysate assay IC50 (μM) | HDAC recombinant enzymatic IC50 (μM) | | % CYP inhibition @ 10 μM: | | CFU % Control remaining @ 10 μM | |
|---|---|---|---|---|---|---|---|---|
| | | | HDAC2 | HDAC1 | 2D6 | 3A4 | Erythroid | Myeloid |
| C | 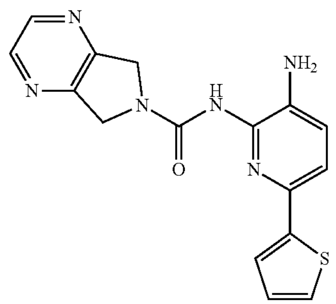 [SMILES: Nc1ccc(-c2cccs2)nc1NC(=O)N1Cc2nccnc2C1] | 0.279 | 0.301 | 0.095 | 0.2 | 1 | 20 | 20 |
| D | 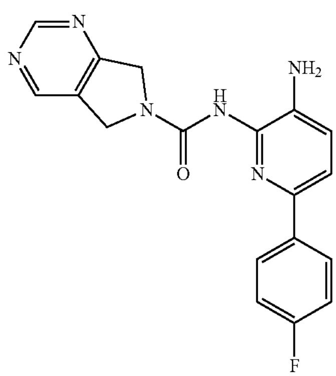 [SMILES: Nc1ccc(-c2ccc(F)cc2)nc1NC(=O)N1Cc2cncnc2C1] | 0.331 | 0.627 | 0.239 | 85 | 2 | 47 | 84 |
| E | 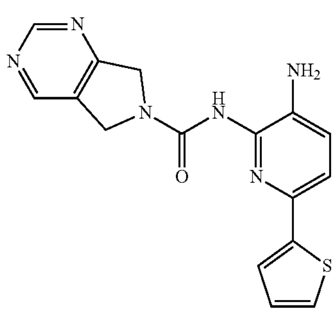 [SMILES: Nc1ccc(-c2cccs2)nc1NC(=O)N1Cc2cncnc2C1] | 0.278 | 0.511 | 0.142 | 50 | −17 | 54 | 83 |
| 2 | 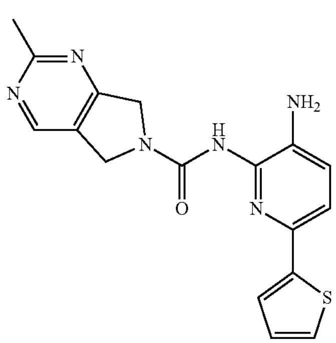 [SMILES: Cc1ncc2c(n1)CN(C(=O)Nc1nc(-c3cccs3)ccc1N)C2] | 0.577 | 0.434 | 0.133 | −5 | 1 | 27 | 59 |

In addition to the substitution between pyrimidine nitrogen atoms improving the CYP inhibition profile of pyrrolopyrimidine compounds, the PK profile of Compound 2 is improved relative to unsubstituted Comparator E as well. See Table 3. The methyl-pyrimidine of Compound 2 provides distinct PK benefits over the unsubstituted pyrimidine analog, displaying a longer half-life, lower clearance, higher bioavailability, and a >5-fold higher brain exposure. These results evidence that slight chemical modifications also produce substantial benefits in PK.

TABLE 3

Comparison in PK profiles of unsubstituted pyrimidine and methyl-substituted pyrimidine matched pairs.

| Structure | Comparator E | Compound 2 |
|---|---|---|
| Mouse IV (1 mpk): T1/2 (hr) | 0.152 | 0.839 |
| Mouse IV (1 mpk): Cl (L/hr/kg) | 8.33 | 4.18 |
| Mouse IV-PO (1/10 mpk): F (%) | 49 | 100 |
| Mouse PO (1/10 mpk): T1/2 (hr) | 0.557 | 1.05 |
| Mouse PO (10 mpk): Brain Cmax (ng/g) (free Cmax, ng/g) | 100 | 583 |
| Mouse PO (10 mpk): Free brain Cmax (ng/g) | 35 | 173 |

Similar advantages were gained by exploring the effects of regioisomers and substitution patterns on pyrrolopyridine ureas of diaminopyridines. For example, while pyrrolopyridine compound Comparator F showed good in vitro potency, it showed high levels of CYP2D6 inhibition and extremely low solubility. See Table 4. Moving the pyridine nitrogen of the pyrrolopyridine (Comparator G) was found to improve solubility. However, both CYP2D6 and CYP3A4 were inhibited at high levels. It was found that adding a methyl substituent adjacent to the pyridine nitrogen of the pyrrolopyridine improved the CYP inhibition profile toward 2D6 and 3A4 somewhat, while maintaining the potency and solubility (Comparator H). The electron withdrawing methoxymethyl substitution adjacent to the pyridine nitrogen (Comparator H) improved the CYP 2D6 and 3A4 inhibition profile even further, again maintaining the desirable potency and solubility profile. Similar results were found between the mono-fluoro and di-fluoro analogues of Comparator I and Compound 1, with Compound 1 displaying slightly reduced solubility. See Table 4.

However, Compound 1 vastly out performed Comparator I with respect to in vitro safety, despite the only one halogen atom difference. See Table 5. A significant benefit was realized in both the erythroid and myeloid progenitor cell lineages upon treatment with the 2,4-difluoro substituted Compound 1 relative to Comparator I.

TABLE 4

Comparison of in vitro profile of Compound 1 to multiple comparators.

| Cmp. | Structure | HDAC2 SY5Y cell lysate assay IC50 (μM) | HDAC recombinant enzymatic IC50 (μM) | | % CYP inhibition @ 10 μM: | | Solubility (μM) |
|---|---|---|---|---|---|---|---|
| | | | HDAC2 | HDAC1 | 2D6 | 3A4 | |
| F | | 0.394 | 0.304 | 0.079 | 62 | −4 | 1 |

TABLE 4-continued

Comparison of in vitro profile of Compound 1 to multiple comparators.

| Cmp. | Structure | HDAC2 SY5Y cell lysate assay IC50 (μM) | HDAC recombinant enzymatic IC50 (μM) | | % CYP inhibition @ 10 μM: | | Solubility (μM) |
|---|---|---|---|---|---|---|---|
| | | | HDAC2 | HDAC1 | 2D6 | 3A4 | |
| G | 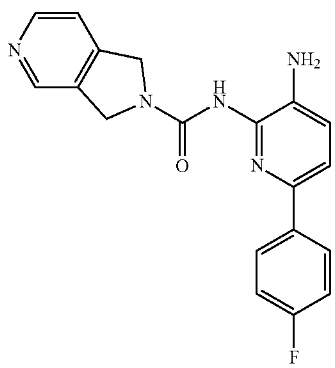 [SMILES: Nc1ccc(-c2ccc(F)cc2)nc1NC(=O)N1Cc2ccncc2C1] | 0.639 | 0.335 | 0.143 | 94 | 65 | 55 |
| H | 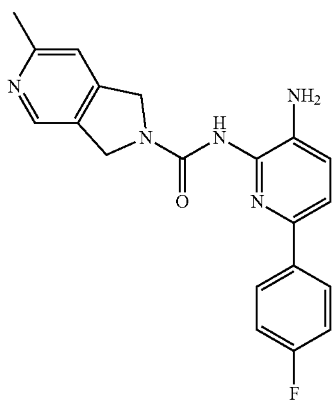 [SMILES: Cc1cc2c(cn1)CN(C(=O)Nc1nc(-c3ccc(F)cc3)ccc1N)C2] | 0.621 | 0.214 | 0.090 | 57 | 28 | 78 |
| I | 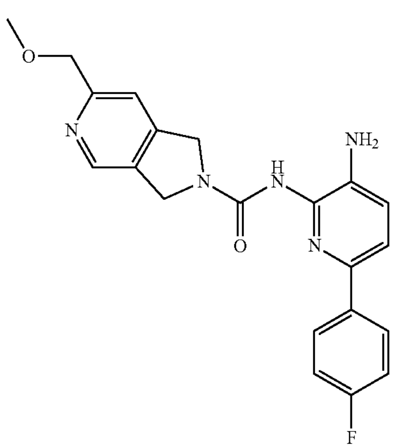 [SMILES: COCc1cc2c(cn1)CN(C(=O)Nc1nc(-c3ccc(F)cc3)ccc1N)C2] | 0.666 | 0.276 | 0.122 | 2 | 33 | 121 |

TABLE 4-continued

Comparison of in vitro profile of Compound 1 to multiple comparators.

| Cmp. | Structure | HDAC2 SY5Y cell lysate assay IC50 (μM) | HDAC recombinant enzymatic IC50 (μM) | | % CYP inhibition @ 10 μM: | | Solubility (μM) |
|---|---|---|---|---|---|---|---|
| | | | HDAC2 | HDAC1 | 2D6 | 3A4 | |
| 1 | 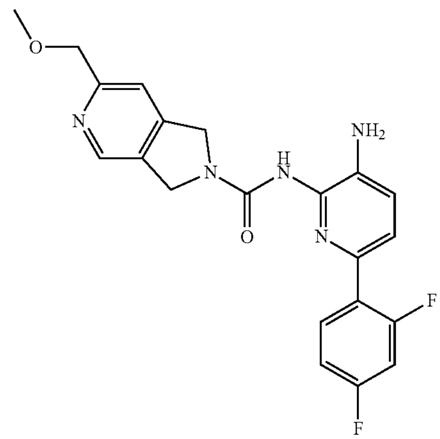 [SMILES: COCc1cc2c(cn1)CN(C(=O)Nc1nc(-c3ccc(F)cc3F)ccc1N)C2] | 0.777 | 0.510 | 0.326 | −1 | 27 | 27 |

TABLE 5

In vitro CFU assay data for Compound 1 and Comparator I

| | Comparator I | Compound 1 |
|---|---|---|
| Structure | | |
| CFU % Control remaining @ 10 μM: Erythroid | 23 | 57 |
| CFU % Control remaining @ 10 μM: Myeloid | 59 | 86 |

Table 6 below shows the results from the brain and plasma exposure following intravenous (IV) and Oral (PO) administration of compounds in mice.

TABLE 6

| | Structure | Projected Brain Cmax @ 10 mpk ng/g (*scaled for comparison) | Projected free brain @ 10 mpk uM (*scaled for comparison) | IV PK T ½ (hr) | IV PK Cl (L/hr/kg) |
|---|---|---|---|---|---|
| Comparator D | 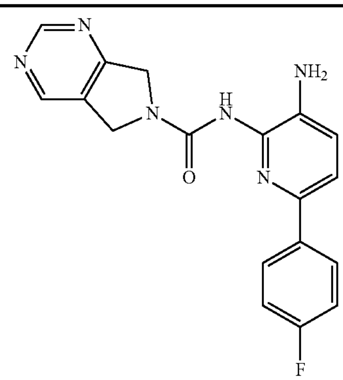 | 158* | 0.111* | Not available | Not available |
| 1 | 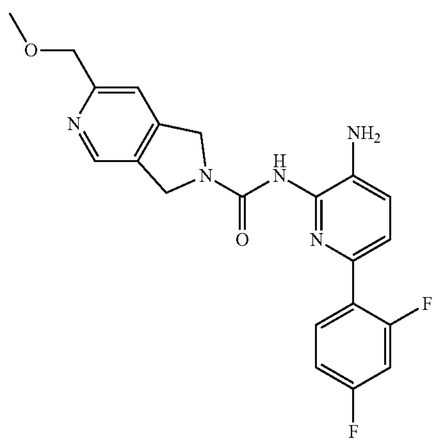 [SMILES: COCc1cc2c(cn1)CN(C(=O)Nc1nc(-c3ccc(F)cc3F)ccc1N)C2] | 2460 | 1.04 | 2.13 PO = 1.97 | 0.681 |

Effects of 14-Days of Oral Treatment with Low Doses of Compounds on Dendritic Spine Morphology in Dorsal Hippocampus (CA1) of Wild Type Mice Compounds were evaluated to determine whether subchronic treatment could produce changes in dendritic spine morphology in the CA1 region of the dorsal hippocampus in wild type (WT) mice. Compounds were administered orally to wild type mice, daily for 14 days. Doses were chosen based on pharmacokinetic data, brain exposure, and potency. Effects of compounds treatments on dendritic spine morphology in the CA1 region of the dorsal hippocampus were then evaluated.

Methods: In-life

Male C57BL/6J mice (7-8-weeks old, n=7 per group) were dosed orally with Rodin compounds or vehicle (20% HPRCD) daily for 14 days. Doses for compounds were chosen based on exposure data from pharmacokinetic experiments. Doses of some compounds were chosen to determine non-efficacious doses, as an extension of earlier studies showing increases in dendritic spine density after treatment with Compound 2 (at doses of 1, 3, 6 and 20 mg/kg/day), Compound 1 (10 mg/kg/day). Mice were sacrificed 24 hours after the last dose, and underwent transcardial perfusion for preparation of brain samples.

Perfusion and Brain Sampling Method

Mice were anesthetized with chloral hydrate (4% chloral hydrate in saline, 10 ml/kg) before undergoing transcardial perfusion with 4% PFA in 1×PBS (pH7.4, room temperature) at 20 mL/min for 54 seconds Immediately after the perfusion, mice were decapitated and their brain extracted. Brains were postfixed in scintillation vials containing 4% PFA (5-10 ml) for 4 min. Brains were sectioned using a tissue vibratome (Leica VT1000) to collect sections (300 μm thick) from the anterior to posterior extremes of each brain.

Ballistic Dye Labeling and Microscopy

Superresolution laser-scanning confocal microscopy (Zeiss LSM880, Airyscan) was performed using a 63× objective (1.42 NA) to scan individually labeled neurons at high resolution (scan resolution =0.06 um μm/pixel; axial resolution =0.06 um μm/focal step). Target neurons were identified in the brain region of interest by epifluorescence navigation using anatomical location and cell morphology. Microscopy was performed blind to experimental conditions. A minimum of 7 mice were tested in each experimental condition. A minimum of 5 samples per mouse (range=5-6) were measured for each segment.

ESP Dendritic Spine Analysis and Assessment of Dendritic Membrane Integrity

Blind deconvolution (AutoQuant) was applied to raw three-dimensional digital images which were then analyzed for spine density and morphology by trained analysts. Individual spines were measured manually for (a) head diameter, (b) length, and (c) neck thickness from image Z-stacks using custom-built Afraxis ESP software. Each dendrite was analyzed by 3 (on average) independent analysts. Automated image assignment software distributed images to analysts in a randomized manner and ensured that each analyst performed measurements of near equal numbers of dendrites per group. Analysts were blinded to all experimental conditions (including treatment, brain region, and cell type). Statistical analysis of interanalyst variability for each dendrite was examined on-line and used to eliminate dendrites that did not meet interanalyst reliability criteria: For spine density and spine morphological classification, data across analysts were averaged to report data for each dendrite.

Dendritic Sampling Positions dHIPP, CA1 Apical 2° (0-50 µm):
Brain region: Dorsal Hippocampus (dHIPP)
Cell type: CA1 pyramidal neuron (CA1)
Branch type: Apical
Branch order: Secondary (2°)
Sample position: 0-50 µm from branchpoint Each identified dendritic spine was measured for (a) spine length, (b) spine head diameter, and (c) neck width. Population distributions of each measure were compiled for each dendritic sample and pooled by group. Raw dendritic spine morphometric values (spine length, head diameter, neck width) were assembled into a scheme used to describe classic spine phenotypes (e.g. mushroom, stubby, etc.). Total spine density was also reported as the sum of the density of all subclasses.

Results

General Observations. The tissue processing demonstrated no observable pathological indications, including abnormal disruption of somatic membranes, dendritic blebbing, or abnormal modifications of dendrite diameters for the target cell type or other cell types within the brain regions tested. For adequate study to study comparisons, total spine density data were normalized to % vehicle levels $$\% \text{ Vehicle} = \frac{(\text{Spine density or } SV2A \text{ puncta})}{(\text{Average Vehicle spine density or } SV2A \text{ puncta})} \times 100 \quad 1)$$

Data were then reported as mean+/−SEM of total spine density (% increase from Vehicle). The results are reported in Table 7.

TABLE 7

Effects on spine morphology in WT mice after 14 days of dosing.

| Compound | Structure | Dose (mg/kg) | Total Spines (% increase over vehicle) | Thin Spines (% increase over vehicle) |
|---|---|---|---|---|
| 1 | 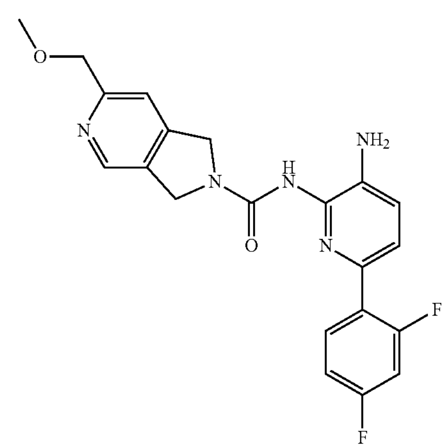 [SMILES: COCc1cc2c(cn1)CN(C(=O)Nc1nc(-c3ccc(F)cc3F)ccc1N)C2] | 0.1 | 12.2 | 13.8 |
| | | 0.3 | 21.3* | 23.2* |
| | | 1 | 34.6* | 45.1* |
| | | 3 | 26.7* | 25.3* |
| | | 10 | 25.1* | 19.9* |

TABLE 7-continued

Effects on spine morphology in WT mice after 14 days of dosing.

| Compound | Structure | Dose (mg/kg) | Total Spines (% increase over vehicle) | Thin Spines (% increase over vehicle) |
|---|---|---|---|---|
| 2 | 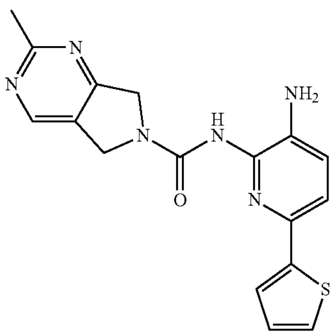 | 0.1 | 8.1 | 11.3 |
| | | 1 | 21.4* | 21.2 |
| | | 3 | 24.7* | 32.2* |
| | | 6 | 15* | 35.4* |
| | | 20 | −0.12 | 37.4* |

*significantly different from vehicle with p value <0.05 using a one-way ANOVA followed by a Dunnett's postHoc analysis The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method of treating a condition in a subject selected from Alzheimer's disease, Huntington's disease, frontotemporal lobar degeneration, Friedreich's ataxia, post-traumatic stress disorder, Parkinson's disease, Parkinson's disease dementia, substance dependence recovery, memory or cognitive function disorder or impairment, neurological disorder with synaptic pathology, disorder of learning distinction, psychiatric disorders, cognitive function or impairment associated with Alzheimer's disease, Lewy body dementia, schizophrenia, Rubinstein Taybi syndrome, Rett Syndrome, Fragile X, multiple sclerosis, age associated memory impairment, age related cognitive decline, and social, cognitive and learning disorders associated with autism, comprising administering to the subject in need thereof an effective amount a histone deacetylase (HDAC) inhibitor of the Formula:

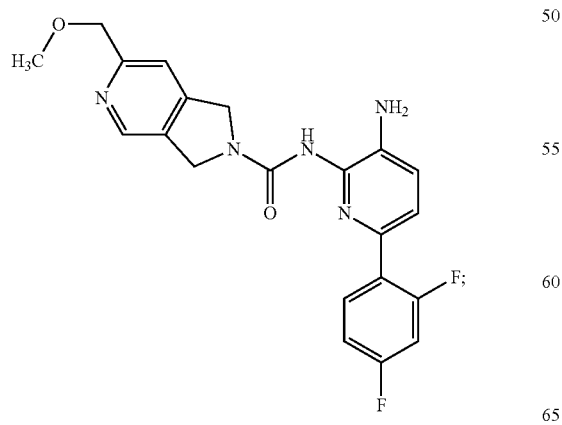

or a pharmaceutically acceptable salt thereof.

2. A method of treating a condition in a subject selected from Alzheimer's disease, Parkinson's disease, Parkinson's disease dementia, Huntington's disease, and Lewy body dementia, comprising administering to the subject in need thereof an effective amount a histone deacetylase (HDAC) inhibitor of the Formula:

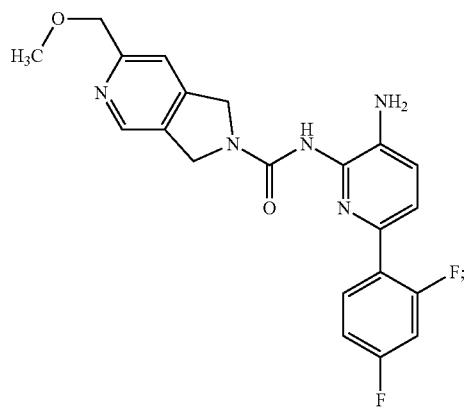 [SMILES: COCc1cc2c(cn1)CN(C(=O)Nc1nc(-c3ccc(F)cc3F)ccc1N)C2]

or a pharmaceutically acceptable salt thereof.

3. A method of inhibiting histone deacetylase (HDAC) activity in a subject comprising the administering to the subject in need thereof an effective amount of a histone deacetylase inhibitor (HDAC) of the Formula:

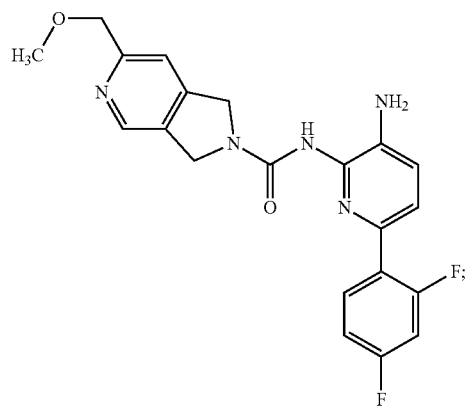 [SMILES: COCc1cc2c(cn1)CN(C(=O)Nc1nc(-c3ccc(F)cc3F)ccc1N)C2]
or a pharmaceutically acceptable salt thereof.
* * * * *